(12) United States Patent
Pointillart et al.

(10) Patent No.: US 8,337,560 B2
(45) Date of Patent: Dec. 25, 2012

(54) INTERVERTEBRAL PROSTHESIS

(76) Inventors: Vincent Pointillart, Bordeaux (FR); Richard Assaker, Kain (BE)

( * ) Notice: Subject to any disclaimer, the term of this patent is extended or adjusted under 35 U.S.C. 154(b) by 198 days.

(21) Appl. No.: 12/681,495

(22) PCT Filed: Oct. 3, 2008

(86) PCT No.: PCT/FR2008/001386
§ 371 (c)(1),
(2), (4) Date: Apr. 5, 2010

(87) PCT Pub. No.: WO2009/074756
PCT Pub. Date: Jun. 18, 2009

(65) Prior Publication Data
US 2010/0217397 A1    Aug. 26, 2010

(30) Foreign Application Priority Data
Oct. 5, 2007    (FR) .................................... 07 06987

(51) Int. Cl.
*A61F 2/44*    (2006.01)
(52) U.S. Cl. .................................................. 623/17.16
(58) Field of Classification Search .... 623/17.11–17.16; 606/247–249
See application file for complete search history.

(56) References Cited

U.S. PATENT DOCUMENTS

| | | | | |
|---|---|---|---|---|
| 4,309,777 A * | 1/1982 | Patil | ........................ | 623/17.13 |
| 5,306,308 A * | 4/1994 | Gross et al. | ................ | 623/17.16 |
| 5,320,644 A * | 6/1994 | Baumgartner | ............ | 623/17.16 |
| 5,545,229 A * | 8/1996 | Parsons et al. | ............ | 623/17.15 |
| 5,674,294 A * | 10/1997 | Bainville et al. | .......... | 623/17.16 |
| 5,676,702 A * | 10/1997 | Ratron | ....................... | 623/17.16 |
| 6,136,031 A * | 10/2000 | Middleton | ................. | 623/17.16 |
| 6,176,882 B1 * | 1/2001 | Biedermann et al. | ..... | 623/17.15 |
| 6,179,874 B1 * | 1/2001 | Cauthen | .................... | 623/17.14 |
| 6,395,035 B2 * | 5/2002 | Bresina et al. | ............ | 623/17.15 |
| 6,579,321 B1 * | 6/2003 | Gordon et al. | ............ | 623/17.16 |
| 7,291,171 B2 * | 11/2007 | Ferree | ........................ | 623/17.11 |
| 7,578,847 B2 * | 8/2009 | Albert et al. | ............... | 623/17.13 |
| 7,959,678 B2 * | 6/2011 | Filippi et al. | ............... | 623/17.14 |
| 8,092,533 B2 * | 1/2012 | Melkent | .................... | 623/17.11 |
| 2001/0016774 A1 * | 8/2001 | Bresina et al. | ............ | 623/17.15 |
| 2007/0191958 A1 * | 8/2007 | Abdou | ........................ | 623/17.16 |
| 2007/0225810 A1 * | 9/2007 | Colleran et al. | .......... | 623/17.13 |
| 2008/0161919 A1 * | 7/2008 | Melkent | .................... | 623/17.11 |
| 2011/0093075 A1 * | 4/2011 | Duplessis et al. | ......... | 623/17.16 |

FOREIGN PATENT DOCUMENTS

| | | |
|---|---|---|
| DE | 2003 15 613 | 12/2003 |
| EP | 1 532 950 | 5/2005 |
| FR | 2 775 891 | 9/1999 |
| FR | 2 787 017 | 6/2000 |
| FR | 2 893 248 | 5/2007 |
| FR | 2 894 808 | 6/2007 |

\* cited by examiner

*Primary Examiner* — Eduardo C Robert
*Assistant Examiner* — Mary Hoffman
(74) *Attorney, Agent, or Firm* — Muncy, Geissler, Olds & Lowe, PLLC

(57) ABSTRACT

An intervertebral disk prosthesis, having a rigid top plate, a rigid bottom plate, and an elastically deformable intermediate cushion housed between the two inner surfaces of the plates. The cushion, at rest, possesses a wedge-shape possessing at least one front notch open into the larger end of the wedge and one rear notch open into the narrower end. The faces of the notches co-operate by contact over an area of magnitude that varies as a function of the intensity and/or direction of the load to which the prosthesis is subjected. The bottoms of the notches are spaced apart from each other and situated in the narrower half of the prosthesis.

16 Claims, 4 Drawing Sheets

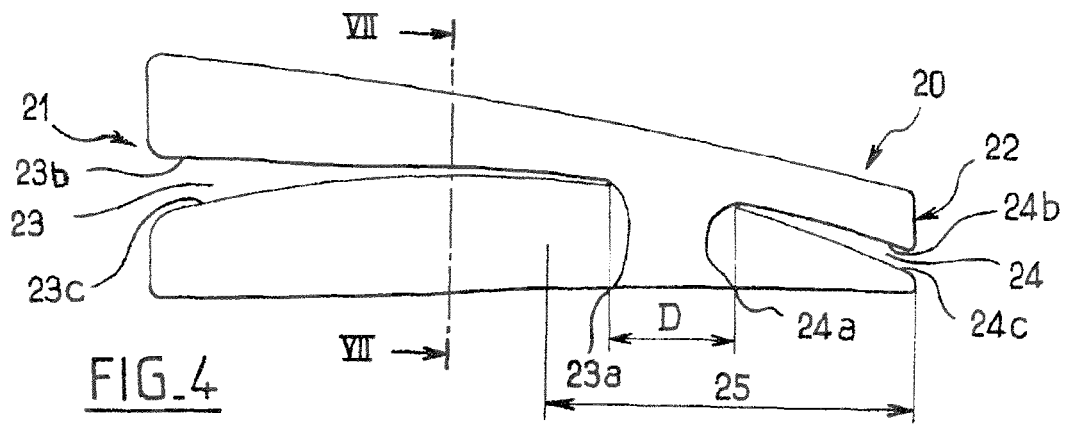
FIG_4
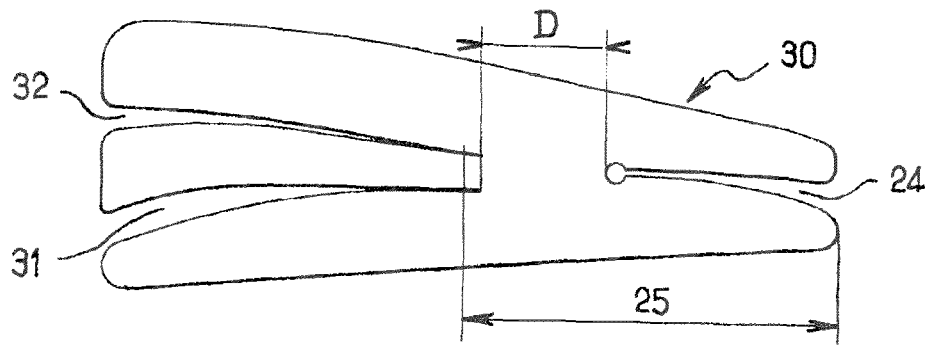
FIG_5
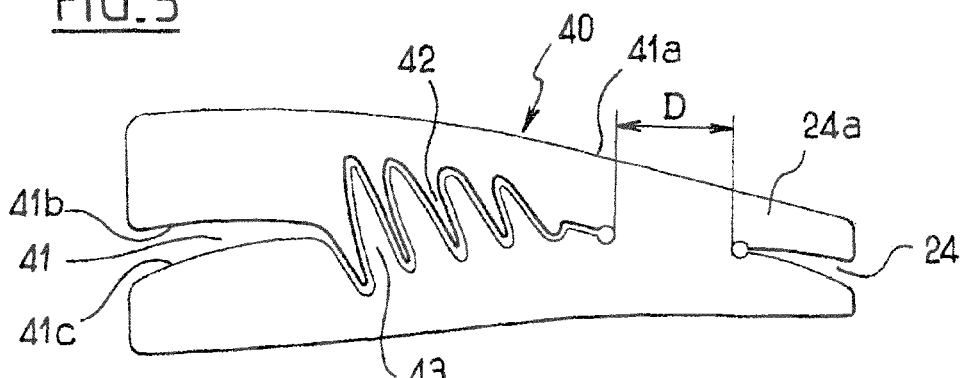
FIG. 6A
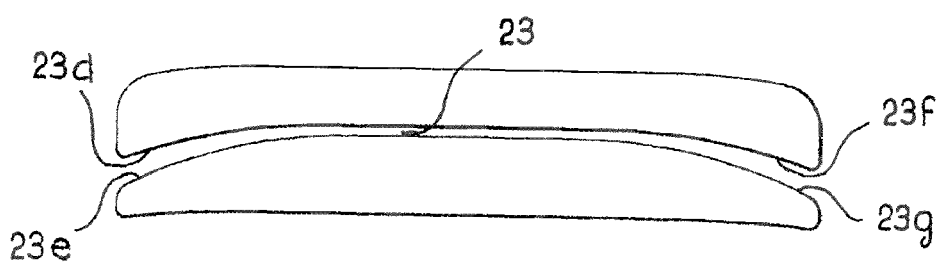
FIG_7

INTERVERTEBRAL PROSTHESIS

The invention relates to an intervertebral disk prosthesis for replacing in full or in part the natural disk that interconnects two vertebrae of the vertebral column, and regardless of which portion of the spine is concerned.

BACKGROUND OF THE INVENTION

Each intervertebral disk of the vertebral column is constituted by a central element referred to as the nucleus pulposus that is enclosed in a roll of fibers referred to as the annulus. The disk interconnects two vertebral bodies and it controls movement of the vertebral column in flexing, inclination, and rotation. The disk can become damaged over time, as a result of effort, or of certain degenerative diseases, and that can give rise to the disk collapsing and/or to it functioning poorly. This can lead to various types of pathology, causing multiple pains of greater or lesser intensity and more or less severe handicaps.

This type of affection is treated by removing the unhealthy disk and replacing it either by an element that is movable or deformable or by an element that rigidly interconnects the two vertebrae in question.

Several types of prosthesis have been proposed for replacing intervertebral disks, but they are only partially satisfactory. They preserve intervertebral mobility and they restore the intervertebral distance to a value close to that ensured by a healthy disk. However in said mobility they impose particular dynamics that are not compatible with, or only partially compatible with the natural relative mobility between two vertebrae. In most situations, the prosthesis imposes dynamics specific thereto, with a center of rotation and various plane-on-plane guidances that inevitably interfere with the natural joint elements that remain between the two vertebrae, in particular the posterior articular facets. In this respect, it should be observed that the care with which a prosthesis is implanted is important since any inaccuracy in its positioning increases the severity of the conflict between the dynamics of the prosthesis and natural dynamics. This non-physiological mobility can give rise to undesirable clinical consequences. It can even be feared that there is a risk of a component migrating or of the prosthetic joint dislocating.

In addition, most known prostheses are unsuitable for restoring normal cervical or lumbar curvature. Restoring the intervertebral distance does not take account of the inclination needed for one vertebra relative to the other in the stack that leads to this curvature, where the existence of such curvature is useful for the normal biomechanics of the entire spine, and more particularly of the adjacent levels.

Furthermore, known prostheses are not adapted to absorbing impacts. A consequence of this inability, associated with the conflict between the natural dynamics and the dynamics of the joint, can lead to premature wear both of natural elements and of prosthetic elements, thereby running the risk of degrading the clinical state of the patient.

An intervertebral disk prosthesis known in particular from WO 2007/057555 comprises:
  a rigid top plate;
  a rigid bottom plate; and
  an elastically compressible intermediate cushion housed between the inner surfaces of the two plates, the assembly having the feature of being subdivided in the thickness direction into two units resting one on the other via complementary contact surfaces. That structure is in the form of a part that does not impose any constrained connection between the two vertebrae it connects together (naturally for amplitudes that correspond to natural relative movements). As a result, the natural guides of such relative movement remain preponderant (in particular the posterior articular facets) and their integrity is preserved. In addition, by appropriately selecting the shape and the state of the contact surfaces, it is possible to control the nature and the concentration of the stresses and the deformations that exist at said surfaces.

OBJECT OF THE INVENTION

The present invention seeks to remedy the drawbacks of conventional prostheses and to constitute a prosthesis that is complementary to the prostheses described in the above-mentioned document while conserving the structural simplicity and ease of implantation thereof.

SUMMARY OF THE INVENTION

To this end, the present invention provides an intervertebral disk prosthesis that comprises:
  a rigid top plate;
  a rigid bottom plate; and
  an elastically deformable intermediate cushion housed between the two inner surfaces of the plates and possessing, at rest, a wedge-shape with at least one front notch open to the larger end of the wedge and a rear notch open to the narrower end, the bottoms of the notches being spaced apart from each other and being situated in the narrower half of the prosthesis, each notch being defined from its bottom by surfaces that extend facing each other and that have contacting zones that vary as a function of the intensity and the direction of the compression load applied to the cushion.

By means of this structure, the connection between the two vertebrae is of two kinds:
  the portion of the cushion that is left intact between the notches is of small dimensions, thereby considerably limiting the stresses that can be transmitted between the vertebrae during relative movements while nevertheless ensuring cohesion at least in compression of the cushion; and
  the notched portions of the cushion that provide contact areas of differing magnitudes depending on the position of the vertebrae relative to each other and depending on the compression exerted on the cushion. These notched portions comprise means for making the deformation behavior of the cushion "variable" as a function of the position and of the load on the vertebrae concerned. The shape and the nature of the faces of these notches that co-operate by coming into contact are factors on which action can be taken during fabrication of the cushion (e.g. by modeling) so as to adjust the behavior of the cushion to match the needs of the patient.

In addition, the wedge-shape of the structure makes it possible to restore the curvature to the spine that is generally degraded by disk degeneration.

By way of example, the cushion is based on high-density polyethylene, on high-density polyurethane, on silicone, or on composites of these various materials.

According to an embodiment feature, each notch is defined by diverging faces such that the area of contact involved in the cushion depends on the extent to which it is flattened, and thus on the position and the load between the two vertebrae in question. In a particular embodiment of the invention, the front notch possesses, between its opening (its edges) and its bottom, two facing faces that define portions in relief that are interleaved. These portions in relief are interpenetrating teeth or interleaved bristles or spikes. This increases the amount of co-operating surface area and its variability as a function of criteria concerning the position and the load on the vertebrae. This particular configuration also makes it possible to have means for acting on more than the quantity of the contacting area since the portions concerned of the cushion have thickness, given the greater or lesser interleaving of the portions in relief while the prosthesis is in use. The properties that can be involved are the properties of a layer of material on either side of the notch and these properties are variable as a function of the degree of interleaving.

In preferred manner, the prosthesis includes a cushion contention membrane fastened to the plates. The contention membrane serves to avoid biological invasion and colonization of the prosthesis. Although all of the materials used are biocompatible, the membrane also serves to isolate the cushion completely from the adjacent biological medium and it forms a barrier against any particles from the cushion migrating into the organism.

The membrane may be a ring fastened to the plates (leaving direct cushion-to-plate contact), or it may be a hermetically sealed bag containing the cushion, and bonded to the plates by adhesive, for example, or indeed it may be a membrane that is sandwiched between each plate and a smaller plate riveted thereto, the other face of said smaller plate being in contact with the cushion.

Other structural arrangements appear on reading the text below. Particular mention is made of the existence of a tie between the two plates of the prosthesis enabling it to be held in a compressed state so as to make it easier to implant. One of the advantages of the prosthesis lies in it being easy to implant without requiring great accuracy since it does not require its degrees of freedom to be "matched" with the natural degrees of freedom that exist between the two vertebrae.

BRIEF DESCRIPTION OF THE DRAWINGS

Other characteristics and advantages of the invention appear from the following description of a few embodiments.

DETAILED DESCRIPTION OF THE INVENTION

Figure 1:
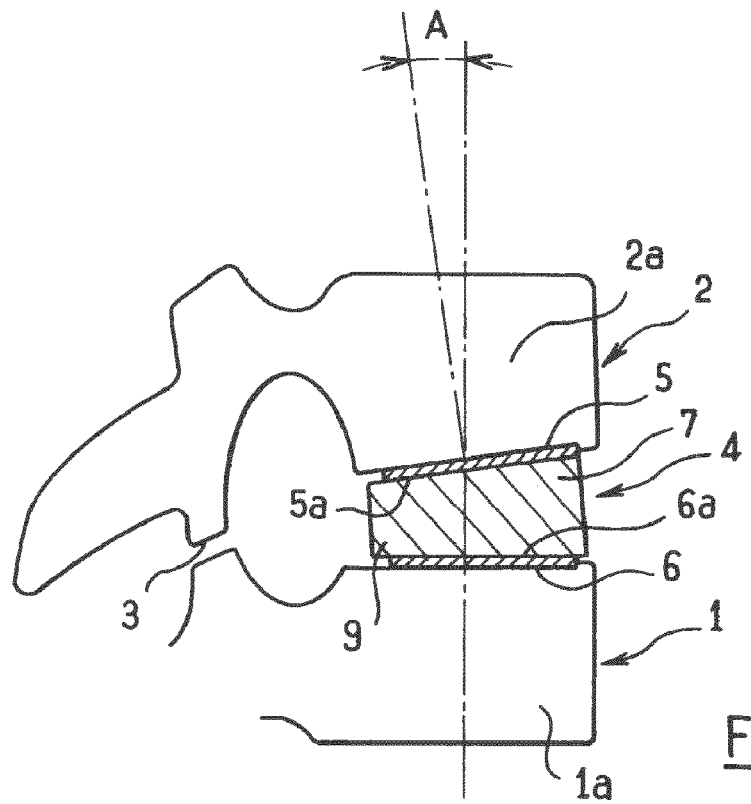
Figure 2:
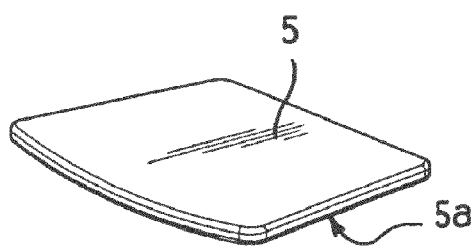
Figure 3:
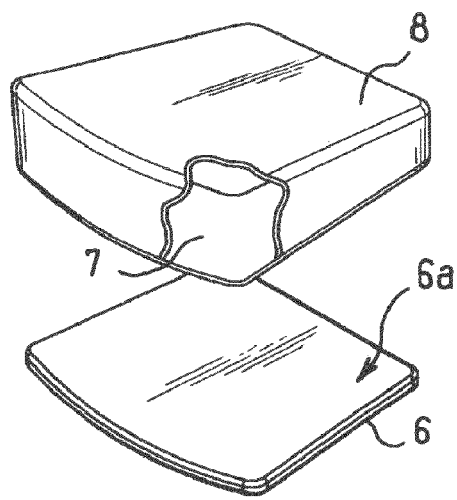
Figure 8:
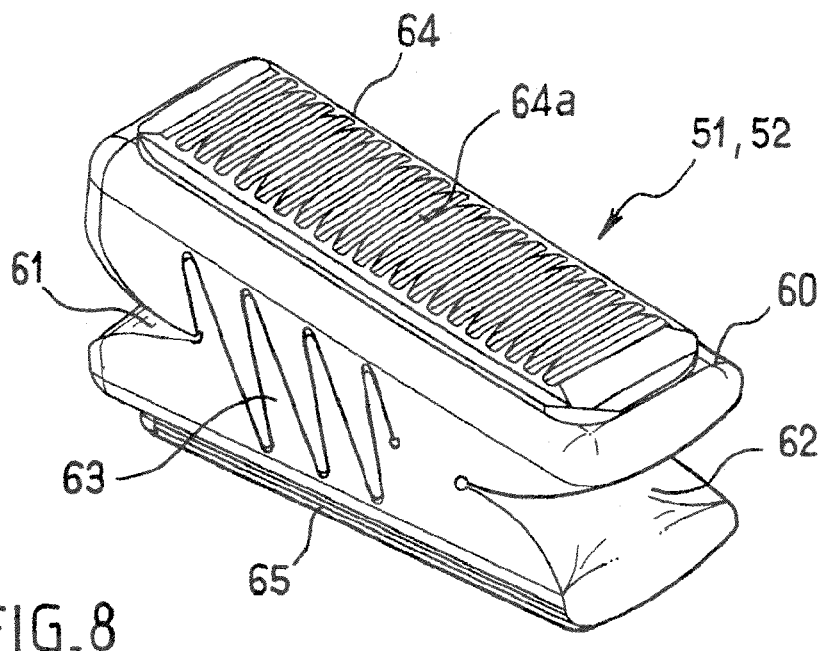

Reference is made to the accompanying drawings, in which:

FIG. 1 is a diagrammatic section view of a prosthesis of the invention placed between two cervical vertebrae;

FIG. 2 is a likewise diagrammatic, exploded view of the prosthesis;

FIG. 3 is a view of the FIG. 2 prosthesis when closed and held compressed by a breakable tie;

FIGS. 4 to 6a, 6b and 6c are antero-posterior section views of three variant embodiments of the deformable cushion used in the prosthesis of the invention;

FIG. 7 is a section view on VII-VII of FIG. 4;

FIG. 8 is an outside view of a lumbar intervertebral half-prosthesis; and

Figure 9:
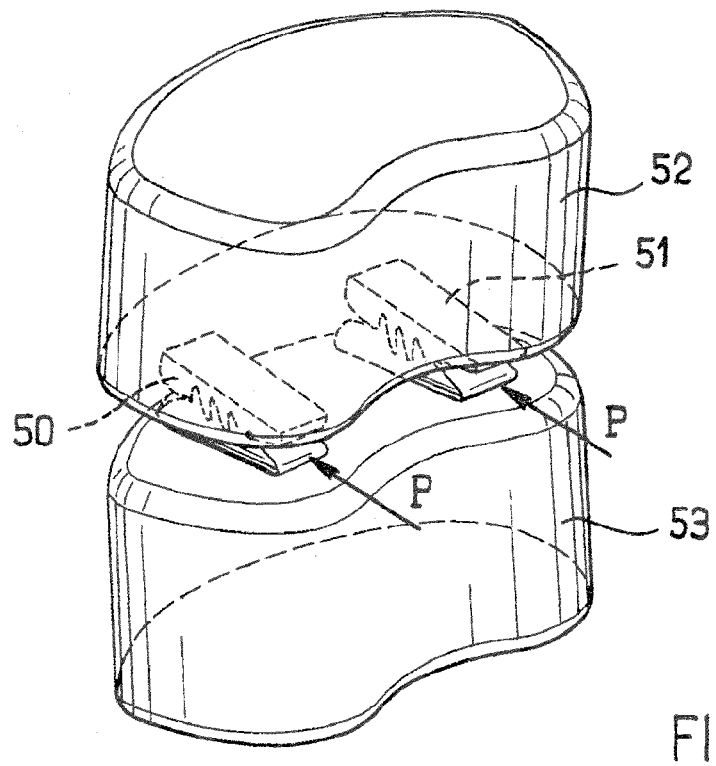

FIG. 9 is a diagram showing the implant between two lumbar vertebral bodies.

DETAILED DESCRIPTION OF THE INVENTION

FIG. 1 shows two successive cervical vertebrae 1 and 2, each having a vertebral body 1a and 2a, and a posterior joint surface 3. Between the vertebral bodies, there is shown diagrammatically a prosthesis 4 that comprises two end plates 5 and 6 and an intermediate body 7 in the form of an elastically deformable cushion, being deformable in particular in compression, and being wedge-shaped with its vertex or edge (the narrower end) to the rear, the right-hand side of the figure showing the anterior zone of the spine.

The end plates 5 and 6 of the prosthesis are in contact with the vertebral bodies 1a and 2a via surfaces on these bodies that have previously been prepared after removing the damaged natural disk. The outside surfaces of these plates may include anchor means, e.g. portions in relief, in order to improve fastening to the bone; fastening may also involve a screw or any equivalent element. The curvature of the spine is represented by the angle A that is imposed by the prosthesis on the relative orientation between these two vertebrae.

In FIG. 2, it can be seen that each of the plates 5 and 6 possesses an inner surface 5a, 6a, here shown as being plane, but that could have a substantially spherical cylindrical concave shape. The compressible cushion 7 is fastened to the plate. The cushion is enclosed in a compression membrane 8 that isolates the cushion biologically from the remainder of the patient's body. The membrane is fastened to the remainder of the prosthesis by any appropriate means. By way of example, mention may be made of a "cylindrical" membrane that is fastened to the edge of each plate (in particular by crimping); the membrane may also be such that its edge is sandwiched between the inner face of each plate and a small plate that is fitted thereto, e.g. by riveting; it may be in the form of a bag that is completely closed with the plate being adhesively bonded thereto.

FIG. 3 shows the prosthesis in its state ready for insertion between two vertebrae, this state corresponding to the compressible cushion 7 being held compressed by a tie 10 that is placed on the anterior face of the prosthesis 4 and that can be broken after the prosthesis has been put into place between the two vertebral bodies 1a and 2a. This tie may also be arranged to surround the entire prosthesis so that breaking it and removing it after cutting it, if necessary, can be performed by the surgeon from behind.

It should be observed in this figure that the plates 5 and 6 are of dimensions such that, in the posterior portion of the prosthesis, they are set back from the cushion, which projects beyond the plate over a portion 9 beside the edge of the wedge.

FIG. 4 is a section view of a first embodiment 20 of the cushion 7 of the invention. The plates are not shown. Like the cushion 7, this cushion is wedge-shaped with its anterior face 21 being larger than its posterior face 22. In its thickness, it is provided with a front notch 23 that is open to the larger end of the wedge and a rear notch 24 that is open to the narrower end, the bottoms 23a and 24a of the notches being spaced apart from each other by a distance D and being situated in the narrower half 25 of the prosthesis, i.e. in the posterior half thereof. Each notch is defined by faces 23b, 23c and 24b, 24c that, when the cushion is not under stress, are spaced apart from each other with progressively-increasing divergence towards the open end thereof into the anterior or posterior face of the prosthesis. This shape constitutes one means for increasing or decreasing the closure of each notch, and thus the dimensions of the contacting surfaces as a function of the degree to which the cushion is compressed in that location. This provides means for determining the behavior of the cushion (flattening and/or deforming) under the effect of loads or movements amongst the adjacent vertebrae.

FIG. 5 shows a corresponding view of a variant embodiment 30 of the cushion in which there are two anterior notches 31 and 32 instead of one. This figure shows the same elements as the preceding figure together with the same references.

In FIG. 6, the cushion 40 possesses an anterior slot 41 that presents a tormented profile between its edges 41b and 41c all the way to its bottom 41a. In this configuration, this profile defines a series of indentations 42 having as their roots the portion of the cushion that lies above the notch 41 and indentations 43 that are formed in the bottom portion of the cushion, these indentations being interleaved in one another with greater or smaller clearance depending on the compression deformation of the cushion. It can also be seen here that this state constitutes means for giving the cushion relationships for varying its behavior in deformation.

Finally, FIG. 7 is a cross-section showing the shape of the anterior notch of the FIG. 4 cushion. It can be seen that in this curved profile plane the notch has its convex side directed upwards and diverging lateral lips 23d, 23e and 23f, 23g.

FIGS. 8 and 9 show most of the elements described above in similar form. Here the prosthesis is made up of two half-prostheses 50 and 51 for inserting between two lumbar vertebral bodies 52 and 53 via a posterior access, i.e. in the direction of arrow P.

In accordance with the invention, each of these half-prostheses comprises a cushion 60 with notches 61 and 62, interleaved indentations 63, a connection zone 64 defined between the bottoms of the notches 61 and 62, and plates 64 and 65, these plates having their outer surfaces textured 64a so as to encourage anchoring of the implant in the vertebral bodies.

Figure 6B:
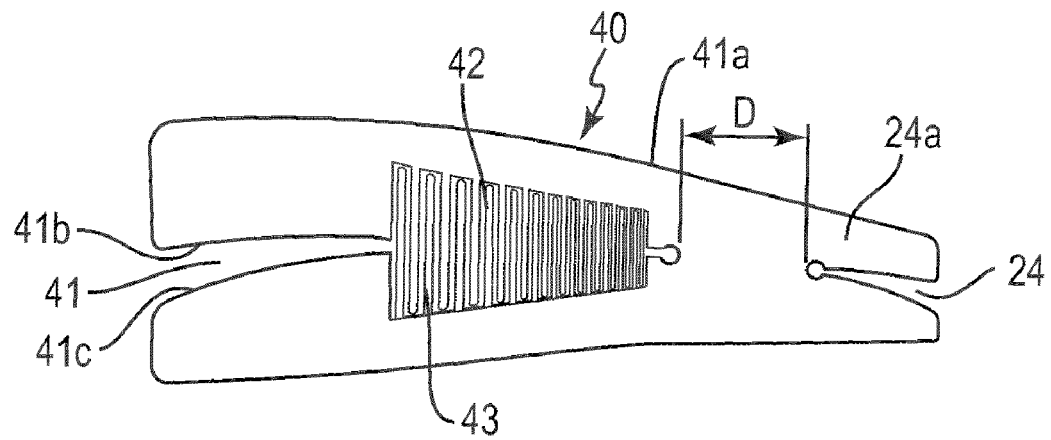
Figure 6C:
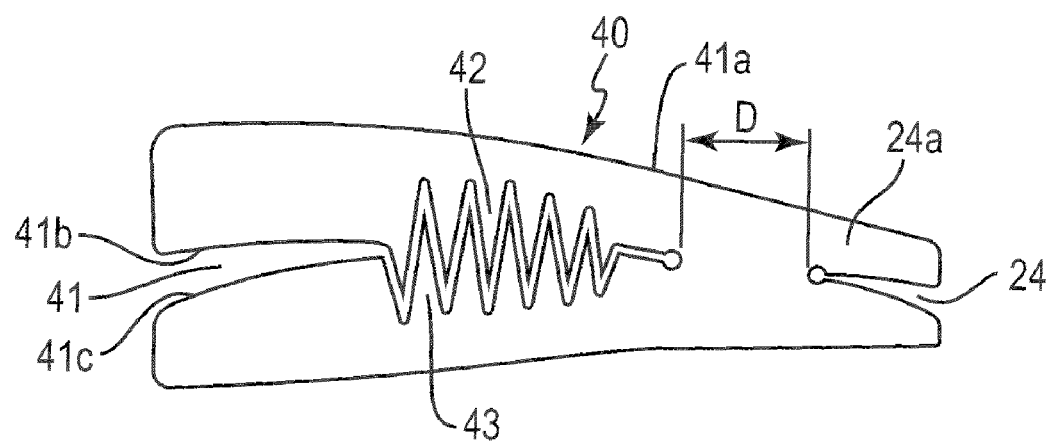

The invention is not limited to the above description given by way of example. Thus, in a variant that is not shown, the indentations are curved, e.g. as circular arcs centered on the posterior side of the implant. In addition, the indentations may be replaced by bristles or spikes, as shown in FIGS. 6b and 6c, that are likewise interleaved amongst one another with more or less vigor so that their resistance to buckling, for example, varies as a function of the degree to which they are interleaved.

What is claimed is:

1. An intervertebral disk prosthesis, comprising:
a rigid top plate having an inner surface;
a rigid bottom plate having an inner surface; and
an elastically deformable intermediate cushion housed between the inner surfaces of the top and bottom plates,
wherein the cushion, at rest, possesses a wedge-shape possessing at least one front notch having opposing faces that open into a larger end of the wedge and one rear notch having opposing faces that open into a narrower end, the faces of the notches co-operating by contact over an area of magnitude that varies as a function of the intensity and/or direction of a load to which the prosthesis is subjected, the notches having bottoms, the bottoms of the notches being spaced apart (D) from each other and being situated in a narrower half of the prosthesis,
wherein the faces of the front notch define portions in relief that are interleaved.

2. The prosthesis according to claim 1, wherein each notch possesses diverging faces.

3. The prosthesis according to claim 1, wherein the portions in relief are interpenetrating teeth.

4. The prosthesis according to claim 1, wherein the portions in relief are interleaved bristles or spikes.

5. The prosthesis according to claim 1, including a compression membrane for the cushion, which membrane is connected to the plates.

6. The prosthesis according to claim 1, including a tie for holding the cushion in the compressed state, which tie is suitable for being cut through after the prosthesis has been put into place.

7. The prosthesis according to claim 1, presenting two substantially parallel anterior notches.

8. The prosthesis according to claim 1, wherein, in front view, at least the anterior notch possesses general curvature with its convex side directed upwards and presents diverging lateral lips.

9. The prosthesis according to claim 1, wherein, for use with lumbar vertebrae, it comprises two identical half-prostheses insertable mutually in parallel between two adjacent vertebral bodies.

10. An intervertebral disk prosthesis, comprising:
a rigid top plate having an inner surface;
a rigid bottom plate having an inner surface; and
an elastically deformable intermediate cushion housed between the inner surfaces of the top and bottom plates,
wherein the cushion, at rest, possesses a wedge-shape possessing at least one front notch having opposing faces that open into a larger end of the wedge and one rear notch having opposing faces that open into a narrower end, the faces of the notches co-operating by contact over an area of magnitude that varies as a function of the intensity and/or direction of a load to which the prosthesis is subjected, the notches having bottoms, the bottoms of the notches being spaced apart (D) from each other and being situated in a narrower half of the prosthesis,
wherein the faces of the front notch define portions in relief that are interleaved, wherein the portions in relief are interpenetrating teeth.

11. The prosthesis according to claim 10, including a compression membrane for the cushion, which membrane is connected to the plates.

12. The prosthesis according to claim 10, including a tie for holding the cushion in the compressed state, which tie is suitable for being cut through after the prosthesis has been put into place.

13. The prosthesis according to claim 10, presenting two substantially parallel anterior notches.

14. The prosthesis according to claim 10, wherein, in front view, at least the anterior notch possesses general curvature with its convex side directed upwards and presents diverging lateral lips.

15. The prosthesis according to claim 10, wherein, for use with lumbar vertebrae, it comprises two identical half-prostheses insertable mutually in parallel between two adjacent vertebral bodies.

16. An intervertebral disk prosthesis, comprising:
a rigid top plate having an inner surface;
a rigid bottom plate having an inner surface; and
an elastically deformable intermediate cushion housed between the inner surfaces of the top and bottom plates,
wherein the cushion, at rest, possesses a wedge-shape possessing at least one front notch having opposing faces that open into a larger end of the wedge and one rear notch having opposing faces that open into a narrower end, the faces of the notches co-operating by contact over an area of magnitude that varies as a function of the intensity and/or direction of a load to which the prosthesis is subjected, the notches having bottoms, the bottoms of the notches being spaced apart (D) from each other and being situated in a narrower half of the prosthesis,
wherein the faces of the front notch define portions in relief that are interleaved, wherein the portions in relief are interleaved bristles or spikes.

* * * * *